(12) United States Patent
Simsch et al.

(10) Patent No.: US 8,877,234 B2
(45) Date of Patent: Nov. 4, 2014

(54) PRESERVATIVES

(75) Inventors: Waltraud Simsch, Kelkheim (DE); Ṗeter Klug, Großostheim (DE); Sonja Klein, Flörsheim (DE)

(73) Assignee: Clariant Finance (BVI) Limited, Tortola (VG)

( * ) Notice: Subject to any disclaimer, the term of this patent is extended or adjusted under 35 U.S.C. 154(b) by 1927 days.

(21) Appl. No.: 11/883,736

(22) PCT Filed: Jan. 25, 2006

(86) PCT No.: PCT/EP2006/000627
§ 371 (c)(1),
(2), (4) Date: Jan. 4, 2008

(87) PCT Pub. No.: WO2006/081969
PCT Pub. Date: Aug. 10, 2006

(65) Prior Publication Data
US 2008/0312195 A1 Dec. 18, 2008

(30) Foreign Application Priority Data

Feb. 3, 2005 (DE) .......................... 10 2005 005 009
Jul. 1, 2005 (DE) .......................... 10 2005 030 762

(51) Int. Cl.
  *A61K 31/197* (2006.01)
  *A61K 31/05* (2006.01)
  *A01N 37/10* (2006.01)
  *A01N 37/36* (2006.01)
  *A61K 47/22* (2006.01)
  *A61K 47/12* (2006.01)
  *A01P 1/00* (2006.01)

(52) U.S. Cl.
  USPC ........... 424/443; 514/159; 514/785; 514/788; 514/566; 514/730; 514/532

(58) Field of Classification Search
  USPC ........................................................ 424/443
  See application file for complete search history.

(56) References Cited

U.S. PATENT DOCUMENTS

| | | | |
|---|---|---|---|
| 4,711,775 A | 12/1987 | Dittmar et al. | |
| 4,797,409 A | 1/1989 | Lohaus et al. | |
| 5,104,645 A * | 4/1992 | Cardin et al. | 514/345 |
| 5,599,800 A | 2/1997 | Candau et al. | |
| 6,107,261 A * | 8/2000 | Taylor et al. | 510/131 |
| 6,121,254 A | 9/2000 | Saint-Leger | |
| 6,447,793 B2 * | 9/2002 | Aust et al. | 424/405 |
| 6,805,874 B1 * | 10/2004 | Lutz et al. | 424/401 |
| 2004/0234482 A1 | 11/2004 | Muller et al. | |

FOREIGN PATENT DOCUMENTS

| | | |
|---|---|---|
| DE | 1 795 270 | 12/1971 |
| DE | 2 214 608 | 10/1973 |
| DE | 2 234 009 | 1/1974 |
| EP | 0 241 918 A2 | 10/1987 |
| EP | 0 646 368 A1 | 4/1995 |
| FR | 2 685 867 A | 7/1993 |
| RU | 2 093 141 C1 | 10/1997 |
| WO | WO 00/06106 A1 | 2/2000 |
| WO | WO 01/06997 A | 2/2001 |

OTHER PUBLICATIONS

PCT International Search Report for PCT/EP2006/000327, dated Apr. 27, 2006.
PCT International Preliminary Report on Patentability for PCT/EP2006/000627, date of completion Jun. 19, 2007.
"Konservierungsmittel und Ibre Praktische Anwendung in Kosmetichen Produkten", Sofw-Journal Seifen, Öle, Fette, Waschse, Verlag fur Chemische Industrie, Augsburg, DE, 116, No. 9/1990, pp. 345-356.
English Abstract for FR 2 685 867, Published Jul. 9, 1993.
English Abstract for RU 2 093 141 C1, Published Oct. 20, 1997.
English Abstract for DE 1 795 270, Published Mar. 18, 1976.
English Abstract for DE 2 214 608, Published Dec. 3, 1973.
"Mixtures of Quaternary Ammonium Compounds and Long-chain Fatty Acids as Antifungal Agents", F. C. Kull, P. C. Eisman, H. D. Sylwestrowicz, and R. L. Mayer, Appl Microbiol. Nov. 1961; 9(6): pp. 538-541.
"Preservatives for Cosmetics", David Steinberg, Allured, Carol Stream, IL, 2006, pp. 12-13.
"Diazolidinyl Urea and Iodopropynyl Butylcarbamate: A Synergistic Blend", Todd Elder, Susan Lindstrom, and Timothy Ravita, Cosmetics and Toiletries, Aug. 1, 1997.

* cited by examiner

*Primary Examiner* — Audrea Buckley
(74) *Attorney, Agent, or Firm* — Tod A. Waldrop

(57) ABSTRACT

The invention relates to clear, liquid preservatives, which contain a) one or several 1-hydroxy-4-methyl-6-alkyl-2(1H)-pyridones and/or one or several salts thereof, wherein alkyl represents a linear, branched or cyclic alkyl group having 1-12 carbon atoms, and b) one or several alcohols containing one or several aromatic groups.

45 Claims, No Drawings

PRESERVATIVES

The present invention relates to clear, liquid compositions comprising 1-hydroxy-4-methyl-6-alkyl-2(1H)-pyridones such as, for example, 1-hydroxy-4-methyl-6-(2,4,4-trimethylpentyl)-2(1H)-pyridone and/or one or more salts thereof and at least one alcohol containing one or more aromatic groups, for the preservation of preparations.

The use of piroctone olamine (2-aminoethanol salt of 1-hydroxy-4-methyl-6-(2,4,4-trimethylpentyl)-2(1H)-pyridone; the commercial product is Octopirox®) and also of 2-phenoxyethanol or benzyl alcohol for preserving cosmetic compositions is known. "Seifen-Öle-Fette-Waschse", 116, No. 9/1990, pp. 345-356 describes how piroctone olamine can be used in shampoos, with sufficient preservation requiring an amount by weight of piroctone olamine of 0.5% to 1%. For O/W, emulsions and W/O emulsions the antimicrobial activity of piroctone olamine used in an amount of 0.5% by weight is inadequate.

In accordance with European Cosmetics Directive 76/768/EEC, ANNEX 6, piroctone olamine can be used in rinse-off products in concentrations of not more than 1% by weight, and in all other cosmetic products in concentrations of not more than 0.5% by weight.

The ease of incorporation of piroctone olamine into cosmetics is restricted by the low solubility of the active substance in water and its no more than moderate solubility in oil.

The object was to provide high-activity preservative compositions for cosmetic, pharmaceutical, and dermatological preparations, said preservative compositions being dermatologically and toxicologically unobjectionable, highly compatible with aqueous systems and with oil systems, having a clear visual appearance, being easy to process, and exhibiting temperature and storage stability.

It has surprisingly been found that this object is achieved by means of clear liquid preservative compositions comprising
a) one or more 1-hydroxy-4-methyl-6-alkyl-2(1H)-pyridones and/or one or more salts thereof, alkyl being a linear, branched or cyclic alkyl group having 1 to 12 carbon atoms and
b) one or more alcohols containing one or more aromatic groups.

The antimicrobial activity, not only of 1-hydroxy-4-methyl-6-alkyl-2(1H)-pyridones such as piroctone olamine, for example, but also of the alcohols containing one or more aromatic groups, is synergistically boosted. The concentrations in which these active antimicrobial substances are used in cosmetic, dermatological, and pharmaceutical products can be lowered significantly as a result.

It has additionally been found that the preservative compositions of the invention are suitable for use in both rinse-off and leave-on products, more particularly in emulsions, preferably in O/W emulsions or W/O emulsions, and produce sufficient preservation of the products at effective piroctone olamine use concentrations of below 0.1% by weight.

Likewise advantageous is the clear appearance of the liquid preservative compositions, and their ease of formulation.

The invention provides clear liquid preservative compositions comprising
a) one or more 1-hydroxy-4-methyl-6-alkyl-2(1H)-pyridones and/or one or more salts thereof, alkyl being a linear, branched or cyclic alkyl group having 1 to 12 carbon atoms, preferably 2,4,4-trimethylpentyl or cyclohexyl, and
b) one or more alcohols containing one or more aromatic groups.

In one preferred embodiment of the invention the preservative compositions of the invention comprise
a) 1-hydroxy-4-methyl-6-(2,4,4-trimethylpentyl)-2(1H)-pyridone and/or one or more salts thereof and
b) one or more alcohols containing one or more, preferably one, aromatic group(s).

In one particularly preferred embodiment the preservative compositions of the invention contain
a) 1-hydroxy-4-methyl-6-(2,4,4-trimethylpentyl)-2(1H)-pyridone and/or one or more salts thereof in amounts by weight of 0.1% to 20%, preferably 1.1% to 10%, more preferably 1.5% to 7%, and with particular preference 5%, and
b) one or more alcohols containing one or more aromatic groups, in amounts by weight of 35% to 99.9% and preferably of 80% to 99.9%.

In a further particularly preferred embodiment the preservative compositions of the invention comprise
a) 1-hydroxy-4-methyl-6-(2,4,4-trimethylpentyl)-2(1H)-pyridone and/or one or more salts thereof,
b) one or more alcohols containing one or more aromatic groups,
c) water,
d) optionally one or more further active antimicrobial substances,
e) optionally one or more hydrotropes, and
f) optionally one or more further additives.

The preservative compositions of the invention comprising one or more 1-hydroxy-4-methyl-6-alkyl-2(1H)-pyridones such as, for example, 1-hydroxy-4-methyl-6-(2,4,4-trimethylpentyl)-2(1H)-pyridone and/or one or more salts thereof, one or more alcohols containing one or more aromatic groups, and water are clear liquids which even after months of storage do not display any crystallization tendencies.

In a further particularly preferred embodiment the preservative compositions of the invention contain
a) 1-hydroxy-4-methyl-6-(2,4,4-trimethylpentyl)-2(1H)-pyridone and/or one or more salts thereof in amounts by weight of 0.1% to 20%, preferably 1.1% to 10%, more preferably 1.5% to 7%, and with particular preference 5%,
b) one or more alcohols containing one or more aromatic groups, in amounts by weight of 35% to 99.8% and preferably of 59.8% to 99.8%, and
c) water in amounts by weight of 0.1% to 35%, preferably 0.1% to 20%, more preferably 0.5% to 5%, and with particular preference 1% to 3%.

The preservative compositions of the invention comprise one or more 1-hydroxy-4-methyl-6-alkyl-2(1H)-pyridones such as, for example, 1-hydroxy-4-methyl-6-(2,4,4-trimethylpentyl)-2(1H)-pyridone and/or one or more salts thereof, it being possible for the salts to be $Li^+$, $Na^+$, $Mg^{++}$, $Ca^{++}$, $Zn^{++}$, $Al^{+++}$, $NH_4^+$, monoalkylammonium, dialkylammonium, trialkyl-ammonium and/or tetraalkylammonium salts, it being possible for the alkyl substituents of the amines independently of one another to be $(C_1-C_{22})$-alkyl radicals or $(C_2-C_{10})$-hydroxyalkyl radicals.

Preference among the stated salts is given to the monoalkylammonium, dialkylammonium, trialkylammonium, and tetraalkylammonium salts.

With particularly preference the preservative compositions of the invention comprise the monoethanolamine salt of 1-hydroxy-4-methyl-6-(2,4,4-trimethylpentyl)-2(1H)-pyridone (Octopirox®, Clariant GmbH).

The alcohols containing one or more aromatic groups that are present in the preservative compositions of the invention are preferably selected from 2-phenoxyethanol, 1-phenoxy- 2-propanol, and benzyl alcohol. Among these alcohols particularly preference is given in turn to 2-phenoxyethanol.

In one further particularly preferred embodiment the preservative compositions of the invention comprise one or more further active antimicrobial substances, preferably in the concentrations of 1% to 25%, more preferably of 5% to 25%, and with particular preference of 10% to 15% by weight. The further active antimicrobial substances are preferably selected from parabens, such as methylparaben, ethylparaben, propylparaben, isopropylparaben, butylparaben, isobutylparaben, sodium methylparaben, sodium ethylparaben, sodium propylparaben, sodium isobutylparaben, sodium isopropylparaben or sodium butylparaben, imidazolidinylurea, diazolidinylurea, iodopropynyl butylcarbamate, 2-bromo-2-nitropropane-1,3-diol, sorbic acid, potassium sorbate, cetyltrimethylammonium chloride, cetylpyridinium chloride, benzethonium chloride, diisobutylethoxyethyldimethylbenzylammonium chloride, diiso-butylphenoxyethoxyethyldimethylbenzylammonium chloride, N-alkyl-N,N-dimethylbenzylammonium chloride, bromide or saccharinate, trimethylammonium chloride, sodium aluminum chlorohydroxylactate, triethyl citrate, tricetylmethylammonium chloride, 2,4,4'-trichloro-2'-hydroxydiphenyl ether (triclosan), 3,4,4'-trichlorocarbanilide (triclocarban), diaminoalkylamide, such as L-lysine hexadecyl amide, DMDM hydantoin, sodium hydroxymethylglycinate, benzoic acid, propionic acid, salicylic acid, 2,4-hexanedienoic acid, 2-hydroxybiphenyl, chlorbutanulum, 3-acetylmethyl-2,4-(3H)pyrandione, formic acid, undecenylic acid, 5-amino-1,3-bis(2-ethylhexyl)-5-methylhexahydro-pyrimidine, 2-bromo-2-nitro-1,3-propanediol, 2,4-dichlorobenzyl alcohol, N-(4-chlorophenyl)-N'-(3,4-dichlorophenyl)urea, 2,4,4'-trichloro-2'-hydroxy-diphenyl ether, poly(hexamethylenediguanide) hydrochloride, 1,2-dibromo-2,4-dicyanobutane, 4,4-dimethyl-1,3-oxazolidine, sodium benzoate, methyl-isothiazolinone, methylchloroisothiazolinone and methylisothiazolinone in a molar ratio of 3:1, chloroxyenol, citrate heavy-metal salts, silver chloride, salicylates such as sodium salicylate, piroctose, more particularly zinc salts, pyrithiones and their heavy-metal salts, more particularly zinc pyrithione, zinc phenol sulfate, farnesol, ketoconazole, oxiconazole, terbinafine, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, and combinations of these active substances.

In one especially preferred embodiment the preservative compositions of the invention comprise one or more further active antimicrobial substances selected from parabens, preferably methylparaben, ethylparaben, propylparaben, butylparaben, isobutylparaben, sodium methylparaben, sodium ethylparaben, sodium propylparaben, sodium isobutylparaben and/or sodium butylparaben, organic acids, preferably sorbic acid, potassium sorbate, salicylic acid, sodium salicylate, benzoic acid and/or sodium benzoate, formaldehyde donors, preferably imidazolidinylurea, diazolidinylurea, DMDM hydantoin and/or sodium hydroxymethylglycinate, and halogenated preservatives, preferably iodopropynyl butylcarbamate and/or 2-bromo-2-nitropropane-1,3-diol.

In one extraordinarily preferred embodiment the preservative compositions of the invention comprise I) aminoethanol salt of 1-hydroxy-4-methyl-6-(2,4,4-trimethylpentyl)-2(1H)-pyridone, 2-phenoxyethanol, and methylparaben or II) aminoethanol salt of 1-hydroxy-4-methyl-6-(2,4,4-trimethylpentyl)-2(1H)-pyridone, 2-phenoxyethanol, and sodium benzoate or III) aminoethanol salt of 1-hydroxy-4-methyl-6-(2,4,4-trimethylpentyl)-2(1H)-pyridone, 2-phenoxyethanol, and benzoic acid or IV) aminoethanol salt of 1-hydroxy-4-methyl-6-(2,4,4-trimethylpentyl)-2(1H)-pyridone, 2-phenoxyethanol, and potassium sorbate or V) aminoethanol salt of 1-hydroxy-4-methyl-6-(2,4,4-trimethylpentyl)-2(1H)-pyridone, 2-phenoxyethanol, and sorbic acid or VI) aminoethanol salt of 1-hydroxy-4-methyl-6-(2,4,4-trimethylpentyl)-2(1H)-pyridone, 2-phenoxyethanol, and sodium salicylate or VII) aminoethanol salt of 1-hydroxy-4-methyl-6-(2,4,4-trimethylpentyl)-2(1H)-pyridone, 2-phenoxyethanol, and salicylic acid.

Where the preservative compositions of the invention comprise one or more active antimicrobial substances selected from salts of organic acids, the preservative compositions of the invention preferably contain from 10% to 35% by weight of water.

In a further particularly preferred embodiment the preservative compositions of the invention comprise one or more antioxidants. The antioxidants preferably selected from superoxide dismutase, tocopherol (vitamin E), ascorbic acid (vitamin C), amino acids (e.g., glycine, histidine, tyrosine, tryptophan) and their derivatives, imidazoles (e.g. urocaninic acid) and their derivatives, peptides such as D,L-carnosine, D-carnosine, L-carnosine, and their derivatives (e.g., anserine), carotenoids, carotenes (e.g. α-carotene, β-carotene, lycopene) and their derivatives, chlorogenic acid and its derivatives, lipoic acid and its derivatives (e.g., dihydrolipoic acid), aurothioglucose, propylthiouracil, and other thiols (e.g., thioredoxin, glutathione, cysteine, cystine, cystamine and their glycosyl, N-acetyl, methyl, ethyl, propyl, amyl, butyl, and lauryl, palmitoyl, oleyl, γ-linoleyl, chlolesteryl, and glyceryl esters) and also salts thereof, dilauryl thiodipropionate, distearyl thiodipropionate, thiodipropionic acid and derivatives thereof (esters, ethers, peptides, lipids, nucleotides, nucleosides, and salts), and also sulfoximine compounds (e.g., buthionine sulfoximine, homocysteine sulfoximine, buthionine sulfones, penta-, hexa-, and heptathionine sulfoximine) in very low tolerated doses (e.g., pmol/kg), additionally (metal) chelators (e.g., α-hydroxy fatty acids, palmitic acid, phytic acid, lactoferrin), α-hydroxy acids (e.g., citric acid, lactic acid, malic acid), humic acid, gallic acid, bile-extracts, bilirubin, biliverdin, EDTA, EGTA, and derivatives thereof, unsaturated fatty acids and their derivatives (e.g., γ-linolenic acid, linoleic acid, oleic acid), folic acid and its derivatives, ubiquinone and ubiquinol and their derivatives, vitamin C and derivatives (e.g., ascorbyl palmitate, Mg ascorbyl phosphate, ascorbyl acetate), tocopherols and derivatives (e.g., vitamin E acetate), vitamin A and derivatives (vitamin A palmitate), coniferyl benzoate of benzoin resin, rutic acid and its derivatives, α-glycosylrutin, ferulic acid, furfurylideneglucitol, carnosine, butylated hydroxytoluene, butylated hydroxyanisole, nordihydroguaic resin acid, nordihydroguaiaretic acid, trihydrobutyro-phenone, uric acid and its derivatives, mannose and its derivatives, zinc and its derivatives (e.g., ZnO, $ZnSO_4$), selenium and its derivatives (e.g., selenomethionine), stilbenes and their derivatives (e.g., stilbene oxide, trans-stilbene oxide) and superoxide dismutase and derivatives suitable in accordance with the invention (salts, esters, ethers, sugars, nucleotides, nucleosides, peptides and lipids) of these stated substances.

Oil-soluble antioxidants may be used with particular advantage for the purposes of the present invention.

With extraordinary preference the preservative compositions of the invention comprise one or more antioxidants selected from tocopheryl acetate, BHT (butylated hydroxytoluene), and EDTA.

The amount of the one or more antioxidants in the preservative compositions of the invention is preferably 0.001% to 30%, more preferably 0.05% to 20%, and with particular preference 0.1% to 5% by weight.

In a further particularly preferred embodiment the preservative compositions of the invention comprise one or more hydrotropes. The hydrotropes are preferably selected from xylene-, toluene- and cumenesulfonate. Cumenesulfonate is particularly preferred.

The weight fraction of the one or more hydrotropes in the compositions of the invention is situated preferably in the range from 1% to 15%, more preferably 4% to 10%, and with particular preference 6% to 8% by weight, based on the completed compositions.

In a further particularly preferred embodiment the preservative compositions of the invention comprise one or more solubilizers, preferably in amounts from 1% to 20% by weight.

Suitable solubilizers include in principle all monohydric or polyhydric alcohols and ethoxylated alcohols, such as ethanol, propanol, isopropanol, n-butanol, isobutanol, glycerol and mixtures thereof, glycols, such as triethylene glycol, butylene glycol, 1,2-propylene glycol, polyethylene glycols having a relative molecular mass below 2000, in particular having a relative molecular mass between 200 and 600, diols, examples being pentanediol, 1,5-pentanediol, 1,6-hexanediol, triacetin (glycerol triacetate), 1-methoxy-2-propanol, and PEG-4 laurate (polyethylene glycol-4 laurate).

With particular preference the preservative compositions of the invention comprise one or more solubilizers selected from triethylene glycol, butylene glycol, and 1,2-propylene glycol.

In one further particularly preferred embodiment the preservative compositions of the invention are composed of
a) 1-hydroxy-4-methyl-6-(2,4,4-trimethylpentyl)-2(1H)-pyridone and/or one or more salts thereof and
b) one or more alcohols containing one or more aromatic groups.

In a further particularly preferred embodiment the preservative compositions of the invention are composed of
a) 1-hydroxy-4-methyl-6-(2,4,4-trimethylpentyl)-2(1H)-pyridone and/or one or more salts thereof and
b) one or more alcohols containing one or more aromatic groups, and
c) water.

The preservative compositions of the invention are advantageously suitable for preserving dermatological, cosmetic, and pharmaceutical products.

The invention therefore further provides for the use of a composition of the invention for preserving dermatological, cosmetic, and pharmaceutical products.

For the purposes of the present invention the dermatological, cosmetic, and pharmaceutical products also include, for example, corresponding formulations.

The dermatological, cosmetic, and pharmaceutical products may for example be aqueous, aqueous-alcoholic, aqueous-surfactant or alcoholic compositions or oil-based compositions, including oil-based compositions in anhydrous form, or emulsions, suspensions or dispersions, more specifically in the form of fluids, foams, sprays, gels, mousses, lotions, creams, powders or wet wipes.

In one preferred embodiment the compositions of the invention are used for preserving wet wipes. In this case the formulation for preservation that is applied to the textile fabric can be an emulsion, more particularly an O/W emulsion, or alternatively a surfactant-based formulation or an oily composition.

In another preferred embodiment the compositions of the invention are used for preserving emulsions.

The emulsions may be water-in-oil emulsions and oil-in-water emulsions, microemulsions, nanoemulsions, and multiple emulsions. The emulsions can be prepared in a known way, in other words for example by cold, hot, hot/cold or PIT emulsification. A particularly preferred embodiment are self-foaming, foam-form, after-foaming or foamable emulsions and micro-emulsions.

The present invention further provides cosmetic, dermatological or pharmaceutical formulations prepared using a preservative composition which comprises
a) one or more 1-hydroxy-4-methyl-6-alkyl-2(1H)-pyridones and/or one or more salts thereof, alkyl being a linear, branched or cyclic alkyl group having 1 to 12 carbon atoms, preferably 2,4,4-trimethylpentyl or cyclohexyl, and with particular preference 2,4,4-trimethylpentyl,
b) one or more alcohols containing one or more aromatic groups, and
c) one or more further active antimicrobial substances,
and cosmetic, dermatological or pharmaceutical formulations which comprise such a preservative composition.

The present invention further provides cosmetic, dermatological or pharmaceutical formulations comprising
a) one or more 1-hydroxy-4-methyl-6-alkyl-2(1H)-pyridones and/or one or more salts thereof, alkyl being a linear, branched or cyclic alkyl group having 1 to 12 carbon atoms, preferably 2,4,4-trimethylpentyl or cyclohexyl, and with particular preference 2,4,4-trimethylpentyl,
b) one or more alcohols containing one or more aromatic groups, and
c) one or more further active antimicrobial substances.

Preference among the formulations specified is given to those in which the one or more active antimicrobial substances of component c) are selected from parabens, preferably methylparaben, ethylparaben, propylparaben, butylparaben, isobutylparaben, sodium methylparaben, sodium ethylparaben, sodium propylparaben, sodium isobutylparaben and/or sodium butylparaben, organic acids, preferably sorbic acid, potassium sorbate, salicylic acid, sodium salicylate, benzoic acid and/or sodium benzoate, formaldehyde donors, preferably imidazolidinylurea, diazolidinylurea, DMDM hydantoin and/or sodium hydroxymethylglycinate, and halogenated preservatives, preferably iodopropynyl butylcarbamate and/or 2-bromo-2-nitropropane-1,3-diol.

Particular preference is given to cosmetic, dermatological or pharmaceutical formulations comprising
a) aminoethanol salt of 1-hydroxy-4-methyl-6-(2,4,4-trimethylpentyl)-2(1H)-pyridone,
b) 2-phenoxyethanol and
c) one or more substances selected from methylparaben, benzoic acid, sodium benzoate, sorbic acid, potassium sorbate, salicylic acid, and sodium salicylate.

In one especially preferred embodiment of the invention the substances of components a), b), and c), based on the completed formulations, are present in the formulations at 0.1% to 2% by weight.

In a further preferred embodiment of the invention the dermatological, cosmetic, and pharmaceutical products are rinse-off products, more particularly shampoos, hair rinses, hair treatments, shower products, including shower gels, or bath foams.

In a further preferred embodiment of the invention the dermatological, cosmetic, and pharmaceutical products are leave-on products, more particularly day creams, night creams, care creams, nutrient creams, body lotions, ointments or lipcare compositions.

Further preferred leave-on products are decorative cosmetics, more particularly makeup, eye shadow, lipstick or mascara products.

In a further preferred embodiment of the invention the dermatological, cosmetic, and pharmaceutical products are sun protection compositions. These compositions comprise one or more organic- or inorganic-based UV filters.

In a further preferred embodiment of the invention the dermatological, cosmetic, and pharmaceutical products are deodorants and antiperspirants, more particularly in the form of sprays, sticks, gels or lotions.

In a further preferred embodiment of the invention the dermatological, cosmetic, and pharmaceutical products are surfactant-free compositions, more particularly surfactant-free solid compositions or surfactant-free emulsions.

The dermatological, cosmetic and pharmaceutical products may comprise, as further auxiliaries and additives, surfactants, emulsifiers, cationic polymers, thickeners, film formers, active antimicrobial substances, astringents, antioxidants, UV light protection filters, pigments/micropigments, gelling agents, and other adjuvants customary in cosmetology, such as superfatting agents, moisturizing agents, silicones, stabilizers, conditioners, glycerol, preservatives, pearlescents, dyes, fragrance oils and perfume oils, solvents, hydrotropes, opacifiers, fatty alcohols, substances having keratolytic and keratoplastic activity, antidandruff agents, active biogenic substances (local anesthetics, antibiotics, antiphlogistics, antiallergics, corticosteroids, sebostatics), vitamins, Bisabolol®, Allantoin®, Phytantriol®, Panthenol®, AHA acids, plant extracts, aloe vera for example, and proteins.

1-Hydroxy-4-methyl-6-(2,4,4-trimethylpentyl)-2(1H)-pyridone and its salts from organic and inorganic acids are obtained by the methods described in EP 241 918, EP 646 368, DE 17 95 270, DE 22 14 608 and DE 22 34 009.

The preservative compositions of the invention can be prepared, for example, by combining the individual components, where appropriate with gentle heating at approximately 35° C.

The examples and applications below are intended to illustrate the invention in more detail, but without confining it to them (all percentages are by weight).

EXAMPLES

Example 1

Preservative Composition 1

| | |
|---|---|
| Octopirox ® | 2% by weight |
| Water | 1% by weight |
| 2-Phenoxyethanol | 97% by weight |

Example 2

Preservative Composition 2

| | |
|---|---|
| Octopirox ® | 5% by weight |
| Water | 2.5% by weight |
| 2-Phenoxyethanol | 92.5% by weight |

Example 3

Preservative Composition 3

| | |
|---|---|
| Octopirox ® | 5% by weight |
| Water | 1% by weight |
| 2-Phenoxyethanol | 94% by weight |

Example 4

Preservative Composition 4

| | |
|---|---|
| Octopirox ® | 10% by weight |
| Water | 5% by weight |
| 2-Phenoxyethanol | 85% by weight |

Example 5

Preservative Composition 5

| | |
|---|---|
| Octopirox ® | 10% by weight |
| Water | 2% by weight |
| 2-Phenoxyethanol | 88% by weight |

Preparation, Examples 1 to 5:

Octopirox® is dissolved with gentle heating (20 to 40° C.) and with stirring in 2-phenoxyethanol. Then water is added with stirring.

Example 6

Preservative Composition 6

| | |
|---|---|
| Octopirox ® | 5% by weight |
| Nipagin ® | 15% by weight |
| Water ® | 2.5% by weight |
| 2-Phenoxyethanol | 77.5% by weight |

Example 7

Preservative Composition 7

| | |
|---|---|
| Octopirox ® | 5% by weight |
| Sodium benzoate | 15% by weight |

-continued

| | |
|---|---|
| Water | 29% by weight |
| 2-Phenoxyethanol | 51% by weight |

Example 8

Preservative Composition 8

| | |
|---|---|
| Octopirox ® | 5% by weight |
| Benzoic acid | 15% by weight |
| Water | 2.5% by weight |
| 2-Phenoxyethanol | 77.5% by weight |

Example 9

Preservative Composition 9

| | |
|---|---|
| Octopirox ® | 5% by weight |
| Potassium sorbate | 15% by weight |
| Water | 25% by weight |
| 2-Phenoxyethanol | 55% by weight |

Example 10

Preservative Composition 10

| | |
|---|---|
| Octopirox ® | 5% by weight |
| Sorbic acid | 10% by weight |
| Propylene glycol | 45% by weight |
| 2-Phenoxyethanol | 40% by weight |

Example 11

Preservative Composition 11

| | |
|---|---|
| Octopirox ® | 5% by weight |
| Sodium salicylate | 15% by weight |
| Water | 21% by weight |
| 2-Phenoxyethanol | 59% by weight |

Example 12

Preservative Composition 12

| | |
|---|---|
| Octopirox ® | 5% by weight |
| Salicylic acid | 15% by weight |
| Water | 2.5% by weight |
| 2-Phenoxyethanol | 77.5% by weight |

Preparation of Examples 6, 8, 10, and 12:

Octopirox® and Nipagin® M and/or the organic acid are dissolved with gentle heating (20 to 40° C.) and with stirring in 2-phenoxyethanol or in a 2-phenoxyethanol/propylene glycol mixture. Then water, where used, is added with stirring.

Preparation of Examples 7, 9 and 11

| | |
|---|---|
| I | The salt of the organic acid is dissolved in water with gentle heating (20 to 40° C.). |
| II | Octopirox ® is dissolved in 2-phenoxyethanol with gentle heating (20 to 40° C.) and with stirring. |
| III | I is added with stirring to II. |

The preservative compositions 1 to 12 are clear liquids.

Storage Stability:

The water-containing preservative compositions are stable at 0° C., 25° C., and 40° C. for a period of 3 months and do not display any crystallization tendency.

TABLE 1

Minimum inhibitory concentrations (MIC) of preservative compositions PC I and PC II in comparison to 2-phenoxyethanol (PE) and Octopirox ®. The compositions of PC I and PC II are set out in table 2

| | PC I MIC in % | % Octopirox ® calculated PC I | % PE calculated PC I | PC II MIC in % | % Octopirox ® calculated PC II | % PE calculated PC II | Octopirox ® MIC in % | PE MIC in % |
|---|---|---|---|---|---|---|---|---|
| *Pseudomonas aeruginosa* | 0.125 | 0.0025 | 0.1225 | 0.031 | 0.0031 | 0.0279 | 0.016 | 0.5 |
| *Staphyloccus aureus* | 0.125 | 0.0025 | 0.1225 | 0.031 | 0.0031 | 0.0279 | 0.002 | 0.25 |
| *Aspergillus niger* | 0.125 | 0.0025 | 0.1225 | 0.016 | 0.0016 | 0.0144 | 0.004 | 0.25 |
| *Candida albicans* | 0.063 | 0.00126 | 0.06174 | 0.016 | 0.0016 | 0.0144 | 0.004 | 0.5 |

The MIC values were determined in accordance with DIN 58940 by the agar dilution method.

The MIC values show that, with the preservative compositions PC I and PC II, composed of the Octopirox® and 2-phenoxyethanol components, specified in table 2, as compared with the individual substances, it is possible to achieve sufficient preservation with substantially lower concentrations employed.

TABLE 2

Preservative compositions PC I and PC II

|  | PC I | PC II |
|---|---|---|
| Octopirox ® [% by weight] | 2 | 10 |
| Phenoxyethanol [% by weight] | 98 | 90 |

Below, the activity of a preservative composition comprising two active components and of various preservative compositions containing 3 active components on different test organisms was ascertained. The results are set out in table 3.

TABLE 3

Activity of preservative compositions PC III to PC VII

| Test organisms | PC III | PC IV | PC V | PC VI | PC VII |
|---|---|---|---|---|---|
| Pseudomonas aeruginosa | A | A | A | A | F |
| Staphylococcus aureus | A | A | A | A | A |
| Candida albicans | A | A | A | A | A |
| Aspergillus niger | A | A | A | A | B |

The evaluations "A" and "B" set out in table 3 were made by analogy with the European Pharmacopeia 5.0, section 5.1.3 Efficacy of antimicrobial preservation. "F" means that the evaluation "A" or "B" was not attained.

The composition of preservative compositions PC III to PC VII is set out in table 4.

TABLE 4

Preservative compositions PC III to PC VII

|  | PC III | PC IV | PC V | PC VI | PC VII |
|---|---|---|---|---|---|
| Octopirox ® [% by weight] | 5 | 5 | 5 | 5 | 5 |
| Nipagin ® M ([% by weight] | 15 | — | — | — | — |
| Benzoic acid (% by weight) | — | 15 | — | — | — |
| Sorbic aicd [% by weight] | — | — | 10 | — | — |
| Salicylic acid [% by weight] | — | — | — | 15 | — |
| Propylene glycol [% by weight] | — | — | 45 | — | — |
| Water [% by weight] | 2.5 | 2.5 | — | 2.5 | 2.5 |
| 2-Phenoxyethanol [% by weight] | 77.5 | 77.5 | 40 | 77.5 | 92.5 |

The activity of preservative compositions PC III to PC VI as compared with PC VII was tested in a surfactant formulation with pH of 7 by means of a preservative loading test. Preservative compositions PC III to PC VII were present in the surfactant formulation at 0.5% by weight in each case. The preservative loading test was carried out and evaluated in accordance with European Pharmacopeia 5.0, section 5.1.3 Efficacy of antimicrobial preservation.

The composition of the surfactant formulation used for the preservative loading tests is as follows:

|  |  |  | % by weight |
|---|---|---|---|
| A | GENAPOL ® LRO paste | (Clariant) | 13.70 |
| B | Water |  | ad 100 |
| C | GENAGEN ® KB | (Clairant) | 6.00 |
|  | Sodium chloride |  | 1.40 |
| D | Citric acid, sodium hydroxide | (10% in water) | 0.08 |

Preparation
I  Mix A and B
II  Add C to I
III  Adjust the pH using D to approximately 7

The results (see table 3) show that with the preservative compositions PC III to PC VI, composed of the Octopirox® and 2-phenoxyethanol components specified in table 4, and also Nipagin® M and water, benzoic acid and water, sorbic acid and propylene glycol or salicylic acid and water, in comparison to the preservative composition PC VII, composed of the Octopirox®, 2-phenoxyethanol and water components specified in table 4, it is possible to achieve a significantly better preservation performance.

FORMULATION EXAMPLES

Example A

Emulsifier-free moisture cream

|  |  |  | % by weight |
|---|---|---|---|
| A | Mineral oil, low-viscosity |  | 6.00 |
|  | Isopropyl palmitate |  | 3.60 |
|  | Soybean oil |  | 2.40 |
| B | Aristoflex ® AVC | (Clariant) | 1.00 |
| C | Water |  | ad 100 |
|  | Glycerol |  | 4.00 |
|  | Preservative composition from example 2 | (Clariant) | 0.50 |
| D | Fragrance |  | 0.30 |

Preparation
I  Mix A and B at room temperature
II  Stir C into I, then add D
III  Homogenize the emulsion Example B O/W night cream

|  |  |  | % by weight |
|---|---|---|---|
| A | Hostaphat ® KW 340 D | (Clariant) | 2.00 |
|  | Hostacerin ® DGMS | (Clariant) | 3.00 |
|  | Stearic acid |  | 2.00 |
|  | Cetyl alcohol |  | 2.00 |
|  | Cetyl palmitate |  | 1.00 |
|  | Lunacera ® M |  | 1.00 |
|  | Miglyol ® 812 |  | 7.00 |
|  | Abil ® 100 |  | 1.00 |
|  | Mineral oil, low viscosity |  | 5.00 |
|  | Jojoba oil |  | 2.00 |
|  | Tocopherol acetate |  | 1.00 |
| B | Carbopol ® 980 |  | 0.20 |

-continued

| | | | |
|---|---|---|---|
| C | Sodium hydroxide (10% in water) | | 0.80 |
| | Glycerol | | 3.00 |
| | Water | | ad 100 |
| | Preservative composition from example 4 | (Clariant) | 0.80 |
| D | Fragrance | | 0.40 |

Preparation
I   Melt A at about 70° C., then add B
II  Heat C to about 70° C.
III Stir II into I and stir before cooling to room temperature
IV  Add D to III at about 35° C.
V   Homogenize the solution

Example C

Emulsion for wet wipes

| | | | % by weight |
|---|---|---|---|
| A | EMULSOGEN ® HCP 049 | (Clariant) | 0.50 |
| | HOSTAPHAT ® KML | (Clariant) | 1.00 |
| | Myritol ® 318 | | 0.50 |
| | Mineral oil, low viscosity | | 0.50 |
| B | Tocopherol acetate | | 0.20 |
| | Panthenol | | 0.50 |
| C | Water | | ad 100 |
| | HOSTAPON ® CLG | (Clariant) | 0.20 |
| | Citric acid (10% in water) | | 0.90 |
| | EDTA, Na salt | | 0.05 |
| | NaOH (10% in water) | | 0.45 |
| | ALLANTOIN | (Clariant) | 0.20 |
| | Preservative composition from example 3 | (Clariant) | 1.00 |

Preparation
I   Add B to A
II  Heat C to about 40° C.
III Add II with stirring to I and stir until cold

Example D

Cream rinse for haircare

| | | | % by weight |
|---|---|---|---|
| A | GENAMIN ® KDMP | (Clariant) | 2.00 |
| | HOSTAPHAT ® KL 340 D | (Clariant) | 1.50 |
| | Cetyl stearyl alcohol | | 2.00 |
| | Liquid paraffin, high viscosity | | 2.00 |
| B | Water | | ad 100.00 |
| | Preservative composition from example 1 | (Clariant) | 0.50 |
| C | Fragrance | | 0.30 |
| | Dye | | q.s. |
| D | Citric acid | | q.s. |

Preparation
I   Melt A at 75° C.
II  Heat B to 75° C.
III Add II to I with stirring
IV  Stir until cold
V   At 35° C. add the components of C to IV
VI  Finally, adjust pH using D to 4

Example E

Shampoo for colored hair

| | | | % by weight |
|---|---|---|---|
| A | UCARE ® Polymer JR-400 | | 0.30 |
| B | Water | | ad 100 |
| C | GENAPOL ® LRO liquid | (Clariant) | 42.90 |
| | GENAGEN ® LAA | (Clariant) | 6.70 |
| | Fragrance | | 0.40 |
| | Dye solution | | q.s. |
| | Preservative composition from example 1 | (Clariant) | 0.75 |
| | GENAGEN ® CAB 818 | (Clariant) | 6.70 |
| | Extrapone Henna Special | | 2.00 |
| | Extrapone Eibisch Special | | 1.00 |
| | Uvinyl MS 40 | | 0.50 |
| D | Citric acid (25% in water) | | q.s. |
| E | Sodium chloride | | 1.00 |

Preparation
I   Dissolve A at 50° C. in B
II  Add the components of C in succession to I
III Adjust the pH using D to 5.5
IV  Finally adjust the viscosity using E

Example F

Conditioner shampoo for hair susceptible to split ends

| | | | % by weight |
|---|---|---|---|
| A | GENAMIN ® BTLF | (Clariant) | 2.00 |
| | GENAPOL ® PMS | (Clariant) | 1.50 |
| | GENAPOL ® LRO liquid | (Clariant) | 35.70 |
| | Glucamate DOE 120 | | 2.50 |
| | Cetyl alcohol | | 0.50 |
| | Sodium chloride | | 0.50 |
| | Sodium cumenesulfonate | | 0.50 |
| B | Water | | ad 100 |
| C | GENAGEN ® CAB 818 | (Clariant) | 6.00 |
| | HOSTAPON ® KCG | (Clariant) | 8.00 |
| D | Dye solution | | q.s. |
| | Preservative composition from example 6 | (Clariant) | 0.60 |
| | Fragrance | | 0.30 |
| | D-Panthenol | | 0.50 |
| | SilCare ® SILICONE 41M15 | (Clariant) | 0.50 |
| E | Sodium chloride | | 0.50 |

Preparation
I   Dissolve and melt components of A in B with stirring and heating to approximately 85° C.
II  Stir until cold
III Add the components of C to II
IV  If necessary adjust the pH
V   Add the components of D to IV
VI  Finally, adjust the viscosity using E

Example G

OW sun lotion

| | | | % by weight |
|---|---|---|---|
| A | HOSTAPHAT ® KL 340 D | (Clariant) | 3.00 |
| | HOSTACERIN ® DGSB | (Clariant) | 5.00 |
| | Liquid paraffin, low-viscosity | | 6.00 |
| | Isopropyl palmitate | | 6.00 |
| | Cetiol ® V | | 6.00 |
| | Neo Heliopan ® AV | | 4.00 |
| | Avocado oil | | 1.00 |
| | Panthenol | | 0.50 |

-continued

| | | | |
|---|---|---|---|
| B | Carbopol ® 980 | | 0.40 |
| C | Sodium hydroxide (10% in water) | | 1.60 |
| | Glycerol | | 3.00 |
| | Water | | ad 100 |
| | Preservative composition from example 7 | (Clariant) | 1.00 |
| D | Fragrance | | 0.30 |

Preparation

| | |
|---|---|
| I | Melt A at about 70° C., then add B |
| II | Heat C to about 70° C. |
| III | Stir II into I and stir until cold |
| IV | Add D to III at about 35° C. |
| V | Finally, homogenize the emulsion |

Example H

| WO sun lotion | | | |
|---|---|---|---|
| | | | % by weight |
| A | HOSTACERIN ® WO | (Clariant) | 2.00 |
| | Arlacel 989 | | 2.00 |
| | Liquid paraffin, low-viscosity | | 10.00 |
| | Eutanol G | | 5.00 |
| | Isopropyl palmitate | | 5.00 |
| | Neo Heliopan ® E 1000 | | 4.00 |
| | Neo Heliopan ® BB | | 1.00 |
| B | Sodium chloride | | 2.00 |
| | Water | | ad 100 |
| | Preservative composition from example 5 | (Clariant) | 0.80 |
| C | Fragrance | | 0.30 |

Preparation

| | |
|---|---|
| I | Melt A at about 80° C. |
| II | Stir the cold solution of B into I |
| III | Stir until cold |
| IV | Add C at about 35° C. to III |

Example I

| WO cream | | | |
|---|---|---|---|
| | | | % by weight |
| A | HOSTACERIN ® WO | (Clariant) | 10.00 |
| | Permulgin ® 3510 | | 4.00 |
| | Liquid paraffin, low-viscosity | | 7.00 |
| | Isopropyl palmitate | | 5.00 |
| | Sunflower oil | | 5.00 |
| | Almond oil | | 3.00 |
| | Wheat germ oil | | 2.00 |
| | Antioxidant | | q.s. |
| B | Water | | ad 100 |
| | Glycerol | | 4.00 |
| | Magnesium sulfate | | 1.00 |
| | Citric acid (10% in water) | | 0.25 |
| | Tetrasodium EDTA | | 0.10 |
| C | Fragrance | | 0.40 |
| | Preservative composition from example 8 | (Clariant) | 0.80 |

Preparation

| | |
|---|---|
| I | Melt A at about 80° C. |
| II | Heat B to about 80° C. |
| III | Stir II into I and stir until cold |
| IV | Add C at about 35° C. to III |

Example J

| OW skin lotion | | | |
|---|---|---|---|
| | | | % by weight |
| A | Hostaphat ® KL 340 D | (Clariant) | 1.00 |
| | Liquid paraffin, low-viscosity | | 8.00 |
| | Isopropyl palmitate | | 3.00 |
| | Cetearyl alcohol | | 0.50 |
| | Myritol ® 318 | | 2.00 |
| | Tegin ® M | | 0.50 |
| | Tocopherol acetate | | 1.00 |
| | SilCare ® Silicone 41M15 | (Clariant) | 1.00 |
| B | Aristoflex ® HMB | | 0.50 |
| C | Water | | ad 100 |
| | Glycerol | | 5.00 |
| D | Fragrance | | 0.30 |
| | Alcohol | | 1.00 |
| | Preservative composition from example 9 | (Clariant) | 0.75 |

Preparation

| | |
|---|---|
| I | Melt A at about 60° C., then add B |
| II | Heat C to about 60° C. |
| III | Stir II into I and stir until cold |
| IV | The components of D are added in succession at about 35° C. to III |
| V | Finally, homogenize the emulsion |

Example K

| Hairstyling cream | | | |
|---|---|---|---|
| | | | % by weight |
| A | Water | | ad 100 |
| | Polyglycol 3000 S | (Clariant) | 1.00 |
| | Propylene glycol | | 1.00 |
| | *Serenoa serrulata* | | 0.30 |
| | Sodium hydroxide (50% in water) | | 0.30 |
| B | Cera alba | | 8.00 |
| | PEG-20 stearate | | 5.00 |
| | Cetearyl alcohol | | 5.00 |
| | Isopropyl myristate | | 5.00 |
| | Ozokerite wax | | 5.00 |
| | Genamin ® KDMP | (Clariant) | 1.50 |
| | Hostaphat ® KL 340 D | (Clariant) | 2.00 |
| C | Diaformer ® Z-651 | (Clariant) | 1.00 |
| | Fragrance | | 0.30 |
| | Preservative composition from example 11 | (Clariant) | 0.90 |

Preparation

| | |
|---|---|
| I | Heat A to about 80° C. |
| II | Heat B to about 80° C. |
| III | Stir I into II and stir until cold |
| IV | At about 35° C. add the components of C to III |

Example L

| Cleansing and care-imparting face wash | | | |
|---|---|---|---|
| | | | % by weight |
| A | Glycerol | | 10.00 |
| | Polyglycol 400 | (Clariant) | 5.00 |
| | Panthenol | | 0.50 |
| | Fragrance | | 0.20 |
| | Preservative composition from example 10 | (Clariant) | 0.80 |
| | ALLANTOIN | (Clariant) | 0.10 |
| | Niacinamide | | 0.10 |
| | Extrapon *Hamamelis* | | 1.00 |

-continued

| | | | |
|---|---|---|---|
| B | Water | | ad 100 |
| C | Aristoflex ® HMB | (Clariant) | 0.30 |

Preparation
I   Dissolve A in B with stirring
II  Add C with stirring to I, stir until homogeneous

Example M

| Body wash lotion | | | |
|---|---|---|---|
| | | | % by weight |
| A | HOSTAPON ® CCG | (Clariant) | 30.00 |
| | Water | | ad 100 |
| B | Glucamate ® DOE 120 | | 2.50 |
| C | GENAGEN ® CAB | (Clariant) | 10.00 |
| | GENAPOL ® PDB | (Clariant) | 3.00 |
| | Fragrance | | 0.30 |
| | Dye solution | | q.s. |
| | Preservative composition from example 12 | (Clariant) | 0.50 |
| D | Citric acid (50% in water) | | 3.30 |
| E | Sodium chloride | | 0.60 |

Preparation
I    Dissolve B with stirring in A, with gentle heating
II   Add the components of C in succession to I
III  Adjust the pH using D
IV   Finally, adjust the viscosity using E

Example N

| Shower gel | | | |
|---|---|---|---|
| | | | % by weight |
| A | GENAPOL ® LRO liquid | (Clariant) | 30.00 |
| B | HOSTAPON ® KCG | (Clariant) | 5.00 |
| | Fragrance | | 0.50 |
| | Cetiol ® HE | | 2.00 |
| C | ALLANTOIN | (Clariant) | 0.40 |
| D | Water | | 52.60 |
| E | GENAGEN ® CAB | (Clariant) | 6.00 |
| | GENAPOL ® L-3 | (Clariant) | 2.00 |
| | Dye solution | | q.s. |
| | Preservative composition from example 6 | (Clariant) | 0.70 |
| F | Sodium chloride | | 1.50 |

Preparation
I    Add the components of B in succession to A
II   Dissolve C in slightly warm D
III  Stir II into I
IV   Add the components of E in succession to III
V    If necessary, adjust the pH
VI   Finally, adjust the viscosity using F

Example O

| Cream rinse for hair care | | | |
|---|---|---|---|
| | | | % by weight |
| A | Genamin ® KDMP | (Clariant) | 1.00 |
| | Genamin ® CTAC | (Clariant) | 2.00 |
| | Hostaphat ® KML | (Clariant) | 1.50 |
| | Cetyl alcohol | | 2.50 |

-continued

| | | | |
|---|---|---|---|
| B | Water | | ad 100 |
| | corresponds to preservative composition from example 12 | (Clariant) | 0.40 |
| C | Fragrance | | 0.30 |
| | Dye solution | | q.s. |
| | Dow Corning 949 | | 1.00 |

Preparation
I    Melt A at about 75° C.
II   Heat B to about 75° C.
III  Add II with stirring to I and then stir until cold
IV   Add the components of C to III at about 30° C.
V    Finally, adjust the pH to 4.0

Example P

| Hair ends fluid | | | |
|---|---|---|---|
| | | | % by weight |
| A | SilCare Silicone ® 41M15 | (Clariant) | 0.30 |
| B | GENAPOL ® LA 070 | (Clariant) | 8.00 |
| C | Glucamate DOE 120 | | 4.00 |
| D | Water | | ad 100 |
| E | Biobranil | | 0.50 |
| | Glycerol | | 2.00 |
| | Panthenol | | 0.50 |
| F | SilCare ® Silicone SEA | (Clariant) | 0.50 |
| | GENAMIN ® CTAC | (Clariant) | 2.00 |
| | corresponds to preservative composition from example 7 | (Clariant) | 0.80 |

Preparation
I    Solubilize A in B
II   Dissolve C in warm D
III  Add II to I
IV   Add the components of E to III
V    At about 35° C., add the components of F with stirring to IV

Example Q

| Hair gel | | | |
|---|---|---|---|
| | | | % by weight |
| A | GENAPOL ® HS 200 | (Clariant) | 0.20 |
| | Fragrance | | 0.20 |
| B | Water | | ad 100 |
| | GENAPOL ® HS 200 | (Clariant) | 1.80 |
| C | Propylene glycol | | 2.00 |
| | Diaformer ® Z-651 | (Clariant) | 4.50 |
| | Alcohol | | 20.00 |
| D | Dye solution | | q.s |
| | Preservative composition from example 2 | (Clariant) | 0.30 |
| E | ARISTOFLEX ® AVC | (Clariant) | 0.80 |

Preparation
I    Mix the components of A
II   Dissolve the components of B with gentle heating. Leave to cool and add to I
III  Add the components of C in succession to II
IV   Add the components of D to III
V    Finally, add E to IV and stir until formulation is homogeneous

Example R

| Styling spray for curly hair | | |
|---|---|---|
| | | % by weight |
| A | Deionized water | ad 100 |
| | Dow Corning 190 surfactant | 0.30 |
| B | Diaformer ® Z-632 (Clariant) | 1.00 |
| | Aristoflex ® A 60 (Clariant) | 1.50 |
| C | Isopropyl alcohol | 45.00 |
| | Fragrance | 0.30 |
| D | Niacinamide | 0.30 |
| | Genamin ® CTAC (Clariant) | 0.50 |
| | Panthenol | 0.20 |
| | Uvinul MS 40 | 0.20 |
| | Merquat 550 | 0.30 |
| | Preservative composition from example 6 (Clariant) | 0.30 |
| E | Citric acid | q.s. |

Preparation
I Thoroughly mix the components of A
II Thoroughly mix the components of B and then add II to I
III Thoroughly mix the components of C and add III to II
IV Add the components of D in succession to III
V Finally, adjust the pH using E to 4.0

INCI names of the commercial products employed:

| | |
|---|---|
| Abil ® 100 | Dimethicone |
| ALLANTOIN | Allantoin |
| Aristoflex ® AVC: | Ammonium Acyloyldimethyltaurate/ VP Copolymer |
| Aristoflex ® A 60 | VA Crotonates Copolymer (and) Isopropyl Alcohol |
| Aristoflex ® HMB | Ammonium Acryloyldimethyl-taurate/Beheneth-25 Methacrylate Crosspolymer |
| Arlacel ® 989 | PEG-7 Hydrogenated Castor Oil |
| Biobranil | Soybean (*Glycine Soja*) Oil (and) Wheat (*Triticum vulgare*) Bran Lipids |
| Carbopol ® 980 | Carbomer |
| Cetiol ® HE | PEG-7 Glyceryl Cocoate |
| Cetiol ® V | Decyloleate |
| Diaformer ® Z-632 | Acrylates/Stearyl Acrylate/ Ethylamine Oxide Methacrylate Copolymer |
| Diaformer ® Z-651 | Acrylates/Lauryl Acrylate/Stearyl Acrylate/Ethylamine Oxide Methacrylate Copolymer |
| Dow Corning ® 190 Surfactant | PEG/PPG-18/18 Dimethicone |
| Dow Corning ® 949 | Amodimethicone (and) Cetrimonium Chloride (and) Trideceth-12 |
| EDTA, Na salt | Disodium EDTA |
| EMULSOGEN ® HCP 049 | PEG-40 hydrogenated Castor Oil, (and) Propylene glycol |
| Eutanol ® G | Octyldodecanol |
| Extrapone Eibisch special | Aqua (and) Ethoxydiglycol (and) Propylene Glycol (and) *Althea Officinalis* Extract (and) Butylene Glycol |
| Extrapone Henna special | Aqua (and) Ethoxydiglycol (and) Propylene Glycol (and) Butylene Glycol (and) Henna (*Lawsonia Inermis*) Extract |
| Genagen ® CAB | Cocamidopropyl Betaine |
| Genagen ® CAB 8181 | Cocamidopropyl Betaine |
| Genagen LAA | Sodium Lauroamphoacetate |
| Genamin ® BTLF | Behentrimonium Chloride |
| Genamin ® CTAC | Cetrimonium Chloride |
| Genamin ® KDMP | Behentrimonium Chloride |
| Genapol ® HS 200 | Steareth-20 |
| Genapol ® LA 070 | Laureth-7 |
| Genapol ® LRO liquid | Sodium Laureth Sulfate |
| Genapol ® L-3 | Laureth-3 |
| Genapol ® PDB | Glycol Distearate (and) Laureth-4 (and) Cocamidopropyl Betaine |
| Genapol ® PMS | Glycol Distearate |
| Glucamate DOE 120 | PEG-120 Methylglucose Dioleate |
| Hostacerin ® DGMS (Clariant) | Polyglyceryl-2 Stearate |
| Hostacerin DGSB | PEG-4 Polyglyceryl-2 Stearate |
| Hostacerin ® WO | Polyglyceryl-2 sesquiisostearate (and) Beeswax (and) Microcrystalline Wax (and) Mineral Oil (and) Magnesium Stearate (and) Aluminum Stearate |
| Hostaphat ® KL 340 D | Trilaureth-4 Phosphate |
| HOSTAPHAT ® KML | Laureth-4 Phosphate (and) Polyglyceryl-2 Sesquiisostearate |
| Hostaphat ® KW 340 D (Clariant) | Tricesteareth-4 Phosphate |
| Hostapon ® CCG | Sodium Cocoyl Glutamate |
| HOSTAPON ® CLG | Sodium Lauroyl Glutamate |
| Hostapon ® KCG | Sodium Cocoyl Glutamate |
| Lunacera ® M | Microcrystalline Wax |
| Merquat 550 | Polyquaternium-7 |
| Miglyol ® 812 | Caprylic/Capric Triglyceride |
| Myritol ® 318 | Caprylic/Capric Triglyceride |
| Neo Heliopan ® AV | Ethylhexyl Methoxycinnamate |
| Neo Heliopan ® BB | Benzophenone-3 |
| Neo Heliopan ® E 1000 | Isoamyl p-Methoxycinnamate |
| Octopirox ® Clariant GmbH | Piroctone Olamine (chemical name: 1-Hydroxy-4-methyl-6-(2,4,4,-trimethylpentyl)-2(1H)-pyridone, 2-aminoethanol salt) |
| Permulgin ® 3510 | Beeswax (and) Mineral Oil (and) Isopropyl myristate |
| Polyglycol 400 | PEG-8 |
| Polyglycol 3000 S | PEG-60 |
| SilCare ® Silicone SEA | Trideceth-9 PG Amodimethicone (and) Trideceth-12 |
| SilCare ® Silicone 41M15 | Caprylyl Trimethicone |
| Uvinyl MS 40 | Benzophenone-4 |

The invention claimed is:

1. A clear liquid preservative composition comprising
   a) 1-hydroxy-4-methyl-6-(2,4,4-trimethylpentyl)-2(1H)-pyridone, a salt of 1-hydroxy-4-methyl-6-(2,4,4-trimethylpentyl)-2(1H)-pyridone, or a mixture thereof in an amount by weight of 0.1% to 20%, and
   b) at least one alcohol selected from the group consisting of: 2-phenoxyethanol, 1-phenoxy-2-propanol, and benzyl alcohol, wherein the at least one alcohol is present in an amount by weight of 35% to 99.9%.

2. The preservative composition according to claim 1, further comprising c) water.

3. The preservative composition of claim 1, further comprising c) water in an amount by weight of 0.1% to 35%.

4. The preservative composition according to claim 1, wherein the salt of 1-hydroxy-4-methyl-6-(2,4,4-trimethylpentyl)-2(1H)-pyridone is the aminoethanol salt.

5. The preservative composition according to claim 1, wherein the at least one alcohol of component b) is 2-phenoxyethanol.

6. The preservative composition according to claim 1, further comprising at least one additional active antimicrobial substance.

7. The preservative composition according to claim 6, wherein the at least one additional active antimicrobial substance is present in an amount of 1% to 25% by weight of the preservative composition.

8. The preservative composition according to claim 7, wherein the at least one additional active antimicrobial substance is selected from the group consisting of: a paraben, an organic acid, a formaldehyde donor, and a halogenated preservative.

9. A preservative composition comprising aminoethanol salt of 1-hydroxy-4-methyl-6-(2,4,4-trimethylpentyl)-2(1H)-pyridone, 2-phenoxyethanol, and methylparaben.

10. The preservative composition according to claim 1, further comprising at least one antioxidant.

11. The preservative composition according to claim 10, wherein the at least one antioxidant is selected from the group consisting of: tocopheryl acetate, BHT, and EDTA.

12. The preservative composition according to claim 1, further comprising at least one hydrotrope.

13. The preservative composition according to claim 12, wherein the at least one hydrotrope is cumenesulfonate.

14. The preservative composition according to claim 1, further comprising at least one solubilizer.

15. The preservative composition according to claim 14, wherein the at least one solubilizer is selected from group consisting of: triethylene glycol, butylene glycol, and 1,2-propylene glycol.

16. A preservative composition consisting of:
   a) 1-hydroxy-4-methyl-6-(2,4,4-trimethylpentyl)-2(1H)-pyridone, a salt of 1-hydroxy-4-methyl-6-(2,4,4-trimethylpentyl)-2(1H)-pyridone, or a mixture thereof and
   b) at least one alcohol selected from the group consisting of: 2-phenoxyethanol, 1-phenoxy-2-propanol, and benzyl alcohol.

17. A preservative composition consisting of:
   a) 1-hydroxy-4-methyl-6-(2,4,4-trimethylpentyl)-2(1H)-pyridone, a salt of 1-hydroxy-4-methyl-6-(2,4,4-trimethylpentyl)-2(1H)-pyridone, or a mixture thereof,
   b) at least one alcohol selected from the group consisting of: 2-phenoxyethanol, 1-phenoxy-2-propanol, and benzyl alcohol, and
   c) water.

18. A method for preserving a dermatological, cosmetic, or pharmaceutical product, comprising the step of adding the preservative composition according to claim 1, to the dermatological, cosmetic, or pharmaceutical product.

19. A method for preserving a wet wipe, comprising the step of contacting the wet wipe with the preservative composition according to claim 1.

20. A method for preserving an emulsion, comprising the step of adding the preservative composition according to claim 1 to the emulsion.

21. A cosmetic, dermatological or pharmaceutical preparation comprising a preservative composition according to claim 1.

22. A cosmetic, dermatological or pharmaceutical formulation comprising
   a) aminoethanol salt of 1-hydroxy-4-methyl-6-(2,4,4-trimethylpentyl)-2(1H)-pyridone,
   b) 2-phenoxyethanol and
   c) at least one substance selected from the group consisting of: benzoic acid, sodium benzoate, sorbic acid, potassium sorbate, salicylic acid, and sodium salicylate.

23. The formulation according to claim 22, wherein components a), b), and c), are present in the formulation at 0.1% to 2% by weight of the completed formulation.

24. The formulation according to claim 22, wherein the formulation is an emulsion.

25. The formulation according to claim 22, wherein the formulation is a surfactant-free emulsion.

26. A clear liquid preservative composition according to claim 1, wherein the 1-hydroxy-4-methyl-6-(2,4,4-trimethylpentyl)-2(1H)-pyridone, the salt of 1-hydroxy-4-methyl-6-(2,4,4-trimethylpentyl)-2(1H)-pyridone, or the mixture thereof is present in an amount of 1.1% to 10% by weight.

27. A clear liquid preservative composition according to claim 1, wherein the 1-hydroxy-4-methyl-6-(2,4,4-trimethylpentyl)-2(1H)-pyridone, the salt of 1-hydroxy-4-methyl-6-(2,4,4-trimethylpentyl)-2(1H)-pyridone, or the mixture thereof is present in an amount of 1.5% to 7% by weight.

28. A clear liquid preservative composition according to claim 1, wherein the 1-hydroxy-4-methyl-6-(2,4,4-trimethylpentyl)-2(1H)-pyridone, the salt of 1-hydroxy-4-methyl-6-(2,4,4-trimethylpentyl)-2(1H)-pyridone, or the mixture thereof is present in an amount of 5% by weight.

29. A clear liquid preservative composition according to claim 1, wherein the at least one alcohol is present in an amount by weight of 80% to 99.9%.

30. The preservative composition according to claim 1, further comprising at least one additional active antimicrobial substance.

31. The preservative composition according to claim 1, further comprising at least one hydrotrope.

32. The preservative composition according to claim 1, further comprising at least one further additive.

33. The preservative composition of claim 1, further comprising water in an amount by weight of 0.1% to 20%.

34. The preservative composition of claim 1, further comprising water in an amount by weight of 0.5% to 5%.

35. The preservative composition of claim 1, further comprising water in an amount by weight of 1% to 3%.

36. The preservative composition according to claim 7, wherein the at least one additional active antimicrobial substance is selected from the group consisting of: methylparaben, ethylparaben, propylparaben, butylparaben, isobutylparaben, sodium methylparaben, sodium ethylparaben, sodium propylparaben, sodium isobutylparaben and sodium butylparaben.

37. The preservative composition according to claim 7, wherein the at least one additional active antimicrobial substance is selected from the group consisting of: sorbic acid, potassium sorbate, salicylic acid, sodium salicylate, benzoic acid and sodium benzoate.

38. The preservative composition according to claim 7, wherein the at least one additional active antimicrobial substance is selected from the group consisting of: imidazolidinylurea, diazolidinylurea, DMDM hydantoin and sodium hydroxymethylglycinate.

39. The preservative composition according to claim 7, wherein the at least one additional active antimicrobial substance is selected from the group consisting of: iodopropynyl butylcarbamate and 2-bromo-2-nitropropane-1,3-diol.

40. A preservative composition comprising aminoethanol salt of 1-hydroxy-4-methyl-6-(2,4,4-trimethylpentyl)-2(1H)-pyridone, 2-phenoxyethanol, and sodium benzoate.

41. A preservative composition comprising aminoethanol salt of 1-hydroxy-4-methyl-6-(2,4,4-trimethylpentyl)-2(1H)-pyridone, 2-phenoxyethanol, and benzoic acid.

42. A preservative composition comprising aminoethanol salt of 1-hydroxy-4-methyl-6-(2,4,4-trimethylpentyl)-2(1H)-pyridone, 2-phenoxyethanol, and potassium sorbate.

43. A preservative composition comprising aminoethanol salt of 1-hydroxy-4-methyl-6-(2,4,4-trimethylpentyl)-2(1H)-pyridone, 2-phenoxyethanol, and sorbic acid.

44. A preservative composition comprising aminoethanol salt of 1-hydroxy-4-methyl-6-(2,4,4-trimethylpentyl)-2(1H)-pyridone, 2-phenoxyethanol, and sodium salicylate.

45. A preservative composition comprising aminoethanol salt of 1-hydroxy-4-methyl-6-(2,4,4-trimethylpentyl)-2(1H)-pyridone, 2-phenoxyethanol, and salicylic acid.

\* \* \* \* \*